United States Patent [19]

Kaplan et al.

[11] 4,189,495
[45] Feb. 19, 1980

[54] 2-METHOXY-BENZAMIDE DERIVATIVES

[75] Inventors: Jean-Pierre Kaplan, Le-Plessis-Robinson; Bernard M. Raizon, Vigneux-sur-Seine; Daniel C. L. Obitz, Orsay; Philippe M. J. Manoury, L'Hay-les-Roses; Henry Najer; Maurice Jalfre, both of Paris; Don P. R. L. Giudicelli, Fontenay-sous-Bois, all of France

[73] Assignee: Synthelabo, Paris, France

[21] Appl. No.: 948,556

[22] Filed: Oct. 4, 1978

Related U.S. Application Data

[60] Division of Ser. No. 749,282, Dec. 10, 1976, Pat. No. 4,158,060, which is a continuation of Ser. No. 641,180, Dec. 16, 1975, Pat. No. 4,021,567.

[30] Foreign Application Priority Data

Oct. 14, 1974 [FR] France ............................... 74 31334
Dec. 18, 1974 [FR] France ............................... 74 41718
Nov. 13, 1975 [JP] Japan .................................. 7534570

[51] Int. Cl.² .................... C07D 207/08; A61K 31/40
[52] U.S. Cl. .................................... 424/274; 424/267; 260/326.47; 542/469; 546/230; 546/233; 546/234
[58] Field of Search ................ 260/326.47; 424/274

[56] References Cited

U.S. PATENT DOCUMENTS

| | | | |
|---|---|---|---|
| 3,342,826 | 9/1967 | Miller et al. | 260/326.47 |
| 3,862,139 | 1/1975 | Podesva et al. | 260/326.47 |
| 3,891,671 | 6/1975 | Thominet | 260/326.47 |
| 3,975,434 | 8/1976 | Bulteau et al. | 260/326.47 |
| 4,021,567 | 5/1977 | Kaplan et al. | 260/326.47 |
| 4,029,673 | 6/1977 | Bulteau et al. | 260/326.47 |

FOREIGN PATENT DOCUMENTS

| | | | |
|---|---|---|---|
| 2212340 | 9/1973 | Fed. Rep. of Germany | 260/326.47 |
| 2358267 | 6/1974 | Fed. Rep. of Germany | 260/326.47 |
| 2442885 | 9/1974 | Fed. Rep. of Germany | 260/326.47 |
| 2417866 | 10/1974 | Fed. Rep. of Germany | 260/326.47 |
| 2452405 | 5/1975 | Fed. Rep. of Germany | 260/326.47 |
| 2556457 | 6/1976 | Fed. Rep. of Germany | 260/326.47 |

Primary Examiner—Mary C. Lee
Attorney, Agent, or Firm—Stevens, Davis, Miller & Mosher

[57] ABSTRACT

The invention provides novel 2-methoxy-benzamide derivatives of the formula:

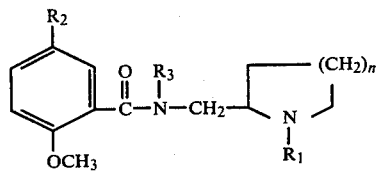

in which n is 1 or 2; $R_1$ represents a cycloalkyl-alkyl radical of formula:

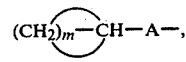

a phenylalkyl radical of formula

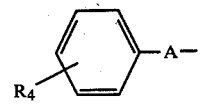

(in which m is an integer from 2 to 5, A is a linear or branched alkylene chain of 1 to 4 carbon atoms, and $R_4$ is hydrogen, halogen, especially fluorine or chlorine, trifluoromethyl, or alkyl or alkoxy of 1 to 3 carbon atoms), $CNCH_2-CH_2-$, $CH\equiv C-CH_2-$,

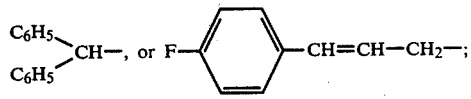

$R_2$ is either chlorine, $SO_2R_5$ (in which $R_5$ is alkyl of 1 to 4 carbon atoms), or $SO_2NR_6R_7$ (in which, $R_6$ and $R_7$, which are identical or different, represent, independently of one another, hydrogen or alkyl of 1 to 4 carbon atoms); and $R_3$ is hydrogen or alkyl of 1 to 4 carbon atoms; in the form of racemates or optical isomers, and their pharmaceutically acceptable acid addition salts, which are useful in the treatment of psychosomatic and pyschotic disturbances.

3 Claims, No Drawings

2-METHOXY-BENZAMIDE DERIVATIVES

This is a division of application Ser. No. 749,282 filed Dec. 10, 1976, now U.S. Pat. No. 4,158,060, which in turn is a continuation of Ser. No. 641,180, filed Dec. 16, 1975, now U.S. Pat. No. 4,021,567, granted May 3, 1977.

The present invention relates to 2-methoxy-benzamide derivatives, their pharmaceutically acceptable acid addition salts, their preparation, and compositions containing them as active principles.

Some 2-methoxy-benzamide derivatives have been described in the literature. For example, French BSM 5916M describes N-pyrrolidinyl-alkyl-benzamides substituted on both the phenyl and the pyrrolidine nuclei, and in particular by a lower alkyl or allyl substituent on the nitrogen atom of the pyrrolidine nucleus. These compounds are anti-emetic agents which however have undesirable side-effects when used in man.

The present invention provides, as new compounds, the 2-methoxy-benzamide derivatives of the formula,

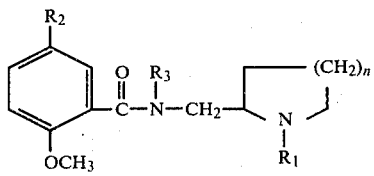
(I)

in which n is 1 or 2; $R_1$ represents a cycloalkyl-alkyl radical of formula:

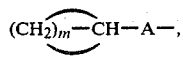

a phenylalkyl radical of formula:

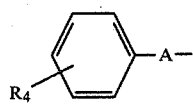

(in which m is an integer from 2 to 5, A is a linear or branched alkylene chain of 1 to 4 carbon atoms, an $R_4$ is hydrogen, halogen, especially fluorine or chlorine, trifluoromethyl, or alkyl or alkoxy of 1 to 3 carbon atoms), $CNCH_2-CH_2-$, $CH\equiv C-CH_2-$,

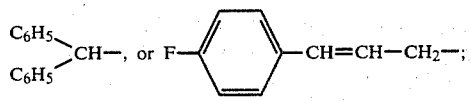

$R_2$ is either chlorine, $SO_2R_5$ (in which $R_5$ is alkyl of 1 to 4 carbon atoms), or $SO_2NR_6R_7$ (in which $R_6$ and $R_7$, which are identical or different, represent, independently of one another, hydrogen or alkyl of 1 to 4 carbon atoms); and $R_3$ is hydrogen or alkyl of 1 to 4 carbon atoms.

$R_1$ is preferably a said phenylalkyl radical in which A is methylene or ethylidene, and especially fluorobenzyl, chlorobenzyl, α-methylbenzyl, methoxybenzyl, trifluromethylbenzyl. Other preferred values of $R_1$ are cyanoethyl, cyclopropylmethyl, phenylethyl, p-chlorophenylethyl, prop-2-ynyl, diphenylmethyl and p-fluorophenyl-vinyl-methyl. $R_2$ is preferably $SO_2NH_2$. $R_3$ is preferably hydrogen or methyl and n is preferably 1.

The compounds of the invention possess an asymmetrical carbon atom and can accordingly exist in the form of racemates or optical isomers, which form part of the invention.

The compounds of the invention can be used in human and veterinary therapy, particularly in the treatment of nervous and psychosomatic disorders.

The compounds of the invention can be prepared by known methods. For example, a halide of a substituted 2-methoxy-benzoic acid, of the general formula (II), can be reacted with an amine of the general formual (III),

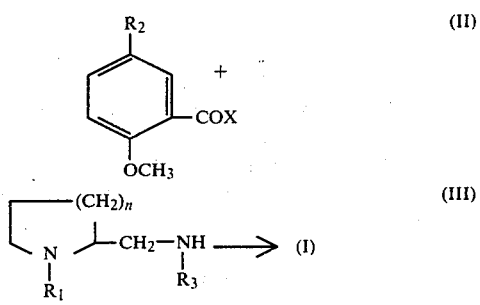

In the above formulae (II) and (III), n, $R_1$, $R_2$ and $R_3$ have the same meanings as in the formula (I) and X represents a halogen, especially chlorine or bromine.

This reaction is preferably carried out at a relatively low temperature ($-5°$ to $+30°$), in a non-polar solvent such as a ketone and in the presence of an alkali metal carbonate.

A possible variant, if $R_3$ represents an alkyl radical, consists of first of all preparing the amide

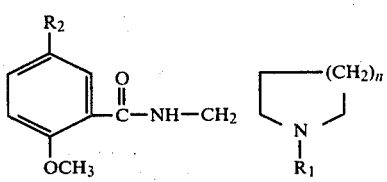

and thereafter attaching the $R_3$ radical to the nitrogen by alkylation.

Another variant consists of attaching the $R_1$ radical to the nitrogen of the heterocyclic nucleus by reaction between the compound of the formula

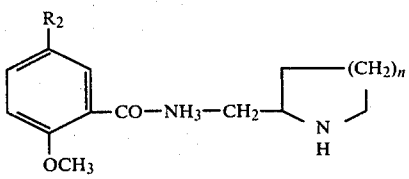

and $R_1X$ (X=an atom of chlorine or of bromine).

The primary amine starting materials are obtained from derivatives of furane and of pyrane, in accordance with the equation given below, which takes account of possible variants:

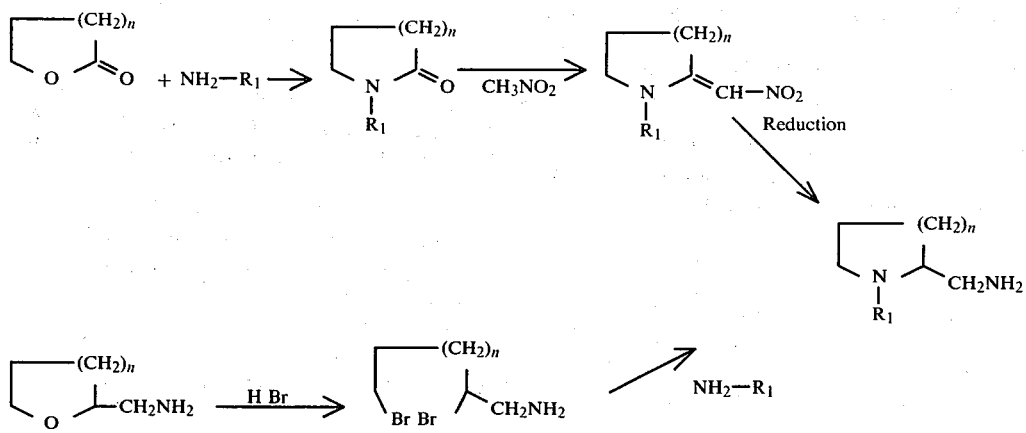

and treating this successively with HBr and $NH_2R_1$. This directly gives the cyclic amine which is disubstituted at the two nitrogens.

Only in the case where $n=1$, there exists another method of preparation of the primary amine starting materials from pyridine derivatives, by ring contraction in accordance with the following equation:

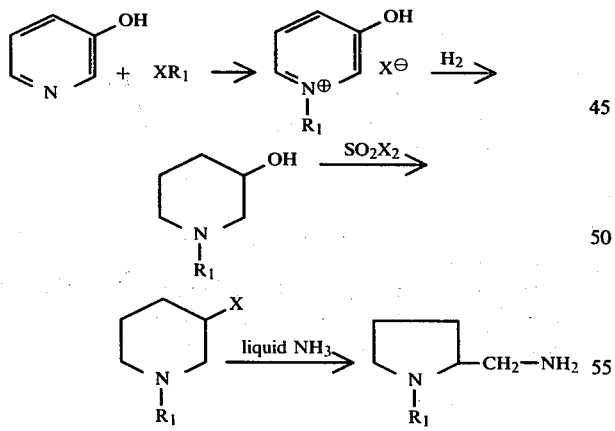

In the above equations, the various symbols have the meanings already defined.

The resolution of the compounds of the invention is effected in accordance with a conventional method; a suitably chosen optically active acid is added to the racemate and the salts thus obtained are separated by making use of the difference in their solubility in an appropriate solvent.

Thus, in the case of dl-N-[1-(p-fluorobenzyl)-pyrrolidinyl-2-methyl]-2-methoxy-5-sulphamoyl-benzamide, a compound of which the preparation will be described later

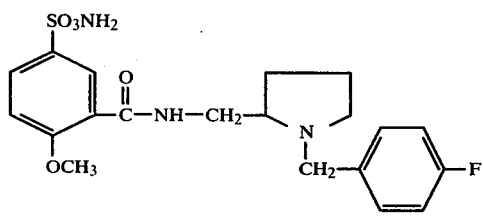

the salts of this base which are most suitable for resolution are the neutral salts (1 molecule of acid and 2 molecules of base) obtained by addition of D- or L-dibenzoyl-tartaric acid.

For simplicity, in the text which follows, the salts will be represented in an abbreviated form, using the following symbols: d or l will represent the optical isomer of the base, that is to say of the compound of the invention, and D or L will represent the optical isomer of the acid used.

The salts of the enantiomers, thus obtained, are separated by utilising the virtual insolubility, in ethanol heated to the reflux temperature, of the salts formed by addition of the acid and the base of the same sign.

The insoluble neutral salts (which hereafter will be represented as follows: d-D-d and l-L-l) are obtained in rather good yields (at least 34% in place of the theoretical maximum of 50%), because the salts of opposite signs (d-L-d and l-D-l) remain in solution in the medium.

Accordingly, if D(+)-dibenzoyltartaric acid is used, the dextro-rotatory base is recovered whilst with L(−)-dibenzoyltartaric acid it is the laevo-rotatory base which is obtained.

Furthermore, it is possible to recover the optical isomer, which proves pharmacologically inactive in the field in question, in order to racemise it. The racemic compound obtained is thereafter resolved to obtain the optical isomer which is of interest.

The examples which follow illustrate the invention.

EXAMPLE 1:
N-[(1-p-fluorobenzyl-pyrrolidinyl-2)-methyl]-2-methoxy-5-sulphamoyl-benzamide

[(I);

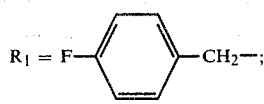

$R_1 = F-\langle\text{phenyl}\rangle-CH_2-;$ $R_2=H_2N-SO_2-$; $R_3=H$; $n=1$; code number: SLC.205]

(a) 1-p-fluorophenyl-pyrrolidin-2-one 47 g (0.376 mol) of p-fluorobenzylamine, 30.4 g (0.353 mol) of furan-2-one and 0.4 g of hydroquinone are introduced into a 125 ml autoclave. After driving the air out of the apparatus by passing a stream of nitrogen through it, the mixture is heated to 250° for 6 hours. It is then cooled and distilled under reduced pressure. 51 g (yield=74.8%) of 1-p-fluorobenzyl-pyrrolidin-2-one are collected as a colourless liquid distilling at 103°–105° under a pressure of 0.01 mm of mercury and solidifying slowly. Melting point=37°–38°.

(b) 1-p-fluorobenzyl-2-nitromethylene-pyrrolidine 26.1 g (0.207 mol) of dimethyl sulphate are added to 40 g (0.207 mol) of 1-p-fluorobenzyl-pyrrolidin-2-one and the mixture is heated to 60° for 4 hours. It is then cooled and a solution of sodium methylate prepared from 4.75 g (0.207 gram atom) of sodium and 100 ml of methanol is introduced slowly, at 0°. When the addition is complete, the mixture is stirred for 30 minutes at 50° C. and again cooled to 0°, and 18.9 g (0.31 mol) of nitromethane are added dropwise whilst continuing the stirring. The reaction mixture is left at ambient temperature for 12 hours and is then heated to 50° for 2 hours. It is cooled, and poured into 500 ml of water, which are then extracted with chloroform. The organic layer is now separated off, washed with water and dried over magnesium sulphate, and the solvent is driven off. The residual product is washed with ether and recrystallised from ethanol. 27 g (55.2% yield) of 1-p-fluorobenzyl-2-nitromethylene-pyrrolidine are thus collected in the form of light yellow crystals melting at 108.5°–109°.

| Analysis: $C_{12}H_{13}FN_2O_2$; | molecular weight: | 236.248 |
|---|---|---|
| Calculated %: | C 61.01; | H 5.55; | N 11.86 |
| Found %: | 60.96 | 5.66 | 12.02 |
| | 61.16 | 5.60 | |

(c) 2-aminomethyl-1-p-fluorobenzyl-pyrrolidine

A solution of 27 g (0.114 mol) of 1-p-fluorobenzyl-2-nitromethylene-pyrrolidine in 600 ml of methanol is hydrogenated at ambient temperature and atmospheric pressure in the presence of Raney nickel. When the theoretical amount of hydrogen has been absorbed, which requires about one hour, the catalyst is filtered off and the methanol is evaporated from the filtrate. The product which remains is distilled under reduced pressure. 17.2 g (yield: 72%) of 2-aminomethyl-1-p-fluorobenzyl-pyrrolidine are collected as a colourless liquid distilling at 80°–82° under a pressure of 0.01 mm of mercury; this product is used, without further purification, in the next stage of the synthesis.

(d) N-[(1-p-fluorobenzyl-pyrrolidinyl-2)-methyl]-2-methoxy-5-sulphamoyl-benzamide 16.5 g (0.079 mol) of 2-aminomethyl-1-p-fluorobenzylpyrrolidine are dissolved in 400 ml of anhydrous acetone. 11 g (0.08 mol) of potassium carbonate are added. The suspension obtained is cooled to 0° and 18 g (0.072 mol) of 2-methoxy-5-sulphamoyl-benzoyl chloride are added dropwise whilst stirring vigorously. The stirring is continued for 1 hour after the end of the addition and the reaction mixture is allowed to return to ambient temperature. The acetone is driven off and the residual product is triturated in a mixture of water and ether; it is then filtered off, washed with water and then with ether, and dried. Thereafter it is dissolved in boiling acetone, animal charcoal is added and the mixture is filtered. The cooled filtrate deposits crystals, which are separated off and dried. 18.5 g (yield=61%) of N-[(1-p-fluorobenzyl-pyrrolidinyl-2)-methyl]-2-methoxy-5-sulpahmoyl-benzamide, melting at 202.5°–203°, are thus obtained.

| Analysis: $C_{20}H_{24}FN_3O_4S$ | (421.494) | | | | |
|---|---|---|---|---|---|
| Calculated %: | C 56.99 | H 5.74 | N 9.97 | F 4.51 | S 7.61 |
| Found %: | 57.06 | 5.66 | 9.93 | 4.37 | 7.98 |
| | 57.19 | 5.68 | 9.89 | | 7.86 |

The methanesulphonate of this compound melts at 216°–217° C. and the hydrochloride at 217°–218° C.

Resolution of the compound obtained, SL-C.205

(a) Isolation of the dextro-rotatory enantiomer of SL-C.205

60 g (0.142 mol) of racemic SL-C.205 are mixed with 53.57 g (0.142 mol) of D-(+)-dibenzoyltartaric acid monohydrate (Fluka Purum) in about 500 ml of methanol. The very slight amount of insoluble matter is filtered off and the filtrate is evaporated to dryness. A semi-crystalline white solid residue is obtained and brought into contact with 1 liter of boiling ethanol. The compound changes very rapidly, in the course of heating at the reflux temperature of the solvent, from the viscous state to the finely crystalline state. When, after several hours' heating at the reflux temperature, there seems to be no further increase in the solid product formed, the latter is filtered off hot on a glass frit kept at 80°. The salt is washed with about 500 ml of boiling ethanol, then with cold ethanol and finally with ether; thereafter it is dried under reduced pressure at 60°.

33.58 g (yield: 39.3%) of the neutral D(+)-dibenzoyltartrate of SLC-205-d, melting at 183°–4°, are thus obtained.

$[\alpha]_D^{25} = +69.9°$ (c=0.6; dimethylformamide).

This compound is again treated in 0.8 l of ethanol and filtered off hot and dried.

29.58 g of the above salt (yield: 34.6%) melting at 183.5°–184° are obtained.

$[\alpha]_D^{25} = +70.6°$ (c=0.6; dimethylformamide).

| Analysis: | | | | | |
|---|---|---|---|---|---|
| Calculated %: | C 57.79 | H 5.18 | N 6.97 | F 3.15 | S 5.32 |
| Found %: | 57.99 | 5.34 | 6.94 | 3.20 | 5.40 |
| | 58.10 | 5.38 | 6.94 | 3.15 | 5.35 |

24 g (0.0199 mol) of the preceding salt are suspended in water and a saturated sodium bicarbonate solution is added; the mixture is then extracted with chloroform and the extract is washed with water, dried over magnesium sulphate in the presence of active charcoal, filtered and evaporated to dryness. A white solid is obtained, which is recrystallised from a mixture of isopropyl ether and ethanol. 14.52 g (yield: 86.5%) of the dextro-rotatory enantiomer of SLC-205; melting at 144.2°–145°, are thus obtained.

$[\alpha]_D^{25} = +91.97°$ (c=0.6; dimethylformamide)

In thin layer chromatography on silica, a single spot (Rf=C.7, eluant=methanol) is obtained.

Analysis:

| Calculated %: | C 56.99 | H 5.74 | N 9.97 |
|---|---|---|---|
| Found %: | 56.99 | 5.51 | 9.95 |
| | 57.00 | 5.47 | 9.96 |

The hydrochloride of this dextro-rotatory compound is laevo-rotatory, $[\alpha]_D^{25} = -12.9°$ (c=0.5; dimethylformamide), and melts at 204.5°–205° C. The methanesulphonate is also laevo-rotatory $[\alpha]_D^{25} = -17.6°$ (c=0.5, dimethylformamide), and melts at 156°–158° C.

(b) Isolation of the laevo-rotatory enantiomer of SLC-205

A mixture of 60 g (0.142 mol) of racemic SLC-205 and of 53.57 g (0.142 mol) of L(−)-dibenzoyltartaric acid monohydrate (Fluka Purum) is dissolved in about 500 ml of methanol. The solution is limpid and the methanol is evaporated to dryness, giving a white semi-crystalline residue. This substance is brought into contact with one liter of hot ethanol, wherein it dissolves rapidly and almost completely.

However, a solid, insoluble and more and more copious precipitate forms very rapidly and continues to develop in spite of vigorous heating at the reflux temperature of the solvent. This heating is continued for 5 hours whilst maintaining efficient stirring and the precipitate is then filtered off hot on a glass frit kept at 80°. The salt is washed with about 500 ml of boiling ethanol, then with cold ethanol and finally with ether. The white powder obtained is dried at 60° under reduced pressure.

33.26 g (yield: 39%) of the neutral L(−)-dibenzoyltartrate of the laevo-rotatory enantiomer of SLC-205, melting with decomposition at 181°–181.5°, are thus obtained.

$[\alpha]_D^{25} = -66.2°$ (c=0.6; dimethylformamide).

This compound is introduced into 0.8 l of ethanol, which is heated to the reflux temperature for 3 hours, whilst stirring; the product is then filtered off hot and washed as before. The salt is obtained in the form of a finely crystalline white powder weighing 30.9 g (yield: 36%) and melting, with decomposition, at 183.5°–184°.

$[\alpha]_D^{25} = -67.3°$ (c=0.6; dimethylformamide).

Analysis:

| Calculated %: | C 57.79 | O 5.18 | H 6.97 | F 3.15 | S 5.32 |
|---|---|---|---|---|---|
| Found %: | 57.99 | 5.40 | 6.87 | 3.21 | 5.40 |
| | 58.25 | 5.31 | 7.03 | 3.18 | 5.35 |

24 g (0.0199 mol) of the L(−)-dibenzoyltartrate of SLC-205-1 are now suspended in water and treated with excess saturated sodium bicarbonate solution. The resulting suspension is extracted with chloroform. The extract is washed with water, dried over magnesium sulphate in the presence of active charcoal, filtered and then evaporated to dryness.

A white crystalline solid, SLC-205-1, is thus obtained, and is recrystallised from a mixture of isopropyl ether and ethanol. 13.73 g of the compound are obtained, representing a yield of 83%. The salt melts at 143.5°–144.5°.

$[\alpha]_D^{25} = -91.6°$ (c=0.65; dimethylformamide).

Thin layer chromatography on silica shows a single spot (Rf=0.7, eluant=methanol).

Analysis:

| Calculated %: | C 56.99 | H 5.74 | N 9.97 |
|---|---|---|---|
| Found %: | 57.07 | 5.73 | 9.73 |
| | 56.84 | 5.85 | 9.77 |

The hydrochloride of this laevo-rotatory compound is dextro-rotatory, $[\alpha]_D^{25} = = +13.2°$ (c=0.5, dimethylformamide) and melts at 204.5°–205° C. The methanesulphonate is also dextro-rotatory $[\alpha]_D^{25} = +18.15°$ (c=0.5, dimethylformamide) and melts at 156°–158° C.

EXAMPLE 2:
N-[(1-p-chlorobenzyl-pyrrolidinyl-2)-methyl]-2-methoxy-5-sulphamoyl-benzamide [(I);

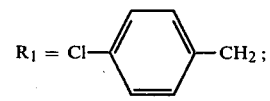

$R_2 = H_2NSO_2$; $R_3 = H$; n=1, code number: SL-C.161]

Using the working method described in Example 1, the following are prepared:

(a) 1-p-chlorobenzyl-pyrrolidin-2-one in a yield of 53%. This compound distills at 148°–150° under a pressure of 0.08 mm of mercury.

Analysis: $C_{11}H_{12}ClNO$ (209.678)

| Calculated %: | C 63.01 | H 5.77 | O 7.63 | N 6.68 | Cl 16.97 |
|---|---|---|---|---|---|
| Found %: | 63.03 | 5.72 | 7.67 | 6.73 | 17.10 |

(b) 1-p-chlorobenzyl-2-nitromethylene-pyrrolidine in a yield of 45%. This compound melts at 145° after recrystallisation from acetone.

Analysis: $C_{12}H_{13}ClN_2O_2$ (262.703)

| Calculated %: | C 56.81 | H 5.56 | N 11.04 | Cl 13.97 |
|---|---|---|---|---|
| Found %: | 57.05 | 5.37 | 11.11 | 14.01 |
| | 56.95 | 5.57 | 11.00 | 14.11 |

(c) 2-aminomethyl-1-p-chlorobenzyl-pyrrolidine

The reduction of the nitromethylene derivative to the amine is carried out slightly differently from that which has been described in Example 1.

500 ml of anhydrous tetrahydrofurane and 23.4 g (0.615 mol) of the double hydride of lithium and aluminium are introduced into a reactor equipped with a mechanical stirrer, and a solution of 27.3 g (0.108 mol) of 1-p-chlorobenzyl-2-nitromethylene-pyrrolidine in 1,000 ml of tetrahydrofurane is then added slowly. The reaction mixture is heated at the reflux temperature for 12 hours and then cooled, and 53 ml of water are added dropwise, followed by 53 ml of 20% strength sodium hydroxide solution and finally 53 ml of water. The precipitate is filtered off and extracted with 500 ml of ether. The ether solution is combined with the filtrate and dried over magnesium sulphate, the solvents are evaporated and the residue is distilled under reduced pressure. 19.5 g (yield: 80.2%) of 2-aminomethyl-1-p-chlorobenzyl-pyrrolidine distilling at 118°–120° under a pressure of 0.06 mm of mercury are obtained.

| Analysis: $C_{12}H_{17}ClN_2$; (224.735) | | | | |
|---|---|---|---|---|
| Calculated %: | C 64.13 | H 7.62 | N 12.46 | Cl 15.78 |
| Found %: | 63.98 | 7.66 | 12.58 | 15.70 |
| | 64.08 | 7.80 | 12.45 | 15.82 |

(d) N-[(1-p-chlorobenzyl-pyrrolidinyl-2)-methyl]-2-methoxy-5-sulphamoyl-benzamide.

Using the method described in Example 1, N-[(1-p-chlorobenzyl-pyrrolidinyl-2)-methyl]-2-methoxy-5-sulphamoylbenzamide, melting at 211° after recrystallisation from methanol, is obtained in a yield of 63.3%.

| Analysis: $C_{20}H_{24}ClN_3O_4S$; (437.949) | | | | | | |
|---|---|---|---|---|---|---|
| Calculated %: | C 54.85 | H 5.52 | O 14.61 | N 9.59 | Cl 8.10 | S 7.32 |
| Found %: | 54.81 | 5.58 | 14.67 | 9.52 | 8.41 | 7.49 |
| | 54.77 | | | 9.44 | 8.54 | 7.45 |

EXAMPLE 3:
N-[(1-benzyl-piperidyl-2)-methyl]-2-methoxy-5-sulphamoyl-benzamide

[(I): $R_1=C_6H_5-CH_2-$; $R_2=H_2NSO_2-$; $R_3=H$; n=2; code number: SL-C-189]

Using the method of Example 1, but replacing the furan-2-one with pyran-2-one and p-fluorobenzylamine by benzylamine, the following are prepared successively:

(a) 1-benzyl-piperid-2-one, distilling at 130° under a pressure of 0.5 mm of mercury (yield: 70.3%).

(b) 1-benzyl-2-nitromethylene-piperidine, melting at 108°–109°, after recrystallisation from methanol (yield: 58%).

| Analysis: $C_{13}H_{16}N_2O_2$; (232.285) | | | | |
|---|---|---|---|---|
| Calculated %: | C 67.22 | H 6.94 | O 13.78 | N 12.06 |
| Found %: | 67.12 | 6.81 | 13.80 | 11.89 |
| | 67.13 | 7.04 | | 11.94 |

(c) 2-aminomethyl-1-benzyl-piperidine, distilling at 115°–120° under a pressure of 0.1 mm (yield: 51.2%).

(d) N-[(1-benzyl-piperidyl-2)-methyl]-2-methoxy-5-sulphamoyl-benzamide, which after two recrystallisations from methanol melts at 168.5°–169°. (Yield: 32%).

| Analysis: $C_{21}H_{27}N_3O_4S$; (417.531) | | | | | |
|---|---|---|---|---|---|
| Calculated %: | C 60.41 | H 6.52 | O 15.33 | N 10.05 | S 7.68 |
| Found %: | 60.58 | 6.58 | 15.03 | 10.04 | 7.87 |
| | 60.48 | 6.61 | 15.20 | | |

EXAMPLE 4:
N-[(1-benzyl-pyrrolidinyl-2)-methyl]-N-methyl-2-methoxy-5-sulphamoyl-benzamide.

(I): $R_1=C_6H_5CH_2$; $R_2=H_2NSO_2-$; $R_3=CH_3$; n=1; code number: SL C 243

(a) N-[(1-benzyl-pyrrolidinyl-2)-methyl]-formamide.

5.10 g (0.11 mol) of 98% strength formic acid are added slowly, whilst stirring and cooling, to 18.45 g (0.097 mol) of 2-aminomethyl-1-benzyl-pyrrolidine, obtained as described in Example 1, with replacement of p-fluorobenzylamine by benzylamine. The mixture is heated slowly to 160° and is kept at this temperature for 20 minutes. It is cooled and the product is fractionated under reduced pressure. After two distillations, 15.3 g (yield: 72.5%) of N-[(1-benzyl-pyrrolidinyl-2)-methyl]-formamide are obtained. Boiling point=165°/0.1 mm of mercury.

(b) 1-benzyl-2-methylaminomethyl-pyrrolidine 8.03 g (0.21 mol) of the double hydride of lithium and aluminium are dissolved in 150 ml of anhydrous ether, and an ether solution of 15.3 g (0.7 mol) of N-[(1-benzyl-pyrrolidinyl-2)-methyl]-formamide is then added dropwise, the speed of the addition being regulated so as to raise the temperature to 35° and then to keep the mixture boiling gently. When the addition is complete, a further 2.8 g (0.074 mol) of lithium aluminium hydride are added and the reaction mixture is heated at the reflux temperature for 4 hours. It is then cooled by means of a bath of iced water and 36 ml of water are introduced gradually so as to hydrolyse the complex formed. The aluminium hydroxide which has precipitated is filtered off and washed copiously with ether; the ether solutions are combined and dried over magnesium sulphate, and the ether is then driven off. The residue is distilled under reduced pressure and 11.5 g (yield: 80.3%) of 1-benzyl-2-methylaminomethyl-pyrrolidine, passing over at 94° to 97° under a pressure of 0.09 mm of mercury, are obtained.

| Analysis: $C_{13}H_{20}N_2$ | (204.317) | | |
|---|---|---|---|
| Calculated %: | C 76.42 | H 9.87 | N 13.71 |
| Found %: | 76.53 | 9.96 | 13.76 |

(c) N-[(1-benzyl-pyrrolidinyl-2)-methyl]-N-methyl-2-methoxy-5-sulphamoyl-benzamide.

7.08 g (0.0509 mol) of potassium carbonate are added to a solution of 8 g (0.0392 mol) of 1-benzyl-2-methylaminomethyl-pyrrolidine in 150 ml of acetone. The mixture is cooled to 0° and a solution of 9.78 g (0.0392 mol) of 2-methoxy-5-sulphamoyl-benzoyl chloride in 100 ml of acetone is introduced dropwise into the suspension, whilst stirring. After the end of the addition, the mixture is allowed to return to ambient temperature and stirring is continued for one hour, after which the mixture is left standing for 12 hours. The inorganic salts which have precipitated are now filtered off and washed copiously with acetone, the acetone solutions are combined and the solvent is driven off. On trituration in petroleum ether, the oily residue solidifies. It is filtered off and dried. It is purified by dissolving it in ethyl acetate, washing the organic solution with water and drying it, evaporating the solvent, extracting the residue with ether in a Soxhlet apparatus, and evaporating the ether. 6.6 g (yield: 40.3%) of N-[(1-benzyl-pyrrolidinyl-2)-methyl]-N-methyl-2-methoxy-5-sulphamoyl-benzamide are thus obtained as an oil which solidifies slowly. Melting point=82°.

| Analysis: $C_{21}H_{27}N_3O_4S$; (417.531) | | | | | |
|---|---|---|---|---|---|
| Calculated %: | C 60.41 | H 6.52 | O 15.33 | N 10.06 | S 7.68 |
| Calculated % (with 0.7% of H₂O determined by the Karl Fischer method): | 59.98 | 6.55 | 15.86 | 9.99 | 7.62 |
| Found %: | 60.30 | 6.79 | 15.84 | 9.77 | 7.54 |
| | 60.20 | 6.80 | | 9.78 | 7.44 |

EXAMPLE 5:
N-[(1-p-fluorobenzyl-pyrrolidinyl-2)-methyl]-2-methoxy-5-chloro-benzamide and its hydrochloride

[(I);

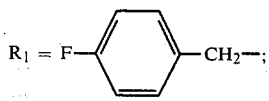

$R_2$=Cl; code number: SL-D.165]

5.62 g (0.027 mol) of 2-aminomethyl-1-p-fluorobenzylpyrrolidine and 4.14 g (0.03 mol) of pulverulent potassium carbonate suspended in 100 ml of anhydrous acetone are introduced into a 250 ml Erlenmeyer flask equipped with a magnetic stirring, a thermometer and a dropping funnel.

A solution of 5.13 g. (0.025 mol) of 5-chloro-2-methoxybenzoyl chloride in 50 ml of anhydrous acetone is then added dropwise whilst stirring and keeping the temperature of the mixture below 10°. This mixture is kept at ambient temperature for 4 hours and is then evaporated under reduced pressure at a temperature not exceeding +30°. The residue is taken up with water and is finally extracted with ether. The ether extract is washed 3 times with water and dried over magnesium sulphate, and the solvent is evaporated. 9.5 g of a residual oil are obtained, and are converted to the hydrochloride by bringing together with a solution of hydrogen chloride gas in ethanol.

4.2 g of 5-chloro-2-methoxy-N-[(1-p-fluorobenzyl-pyrrolidinyl-2)-methyl]-benzamide hydrochloride, which after successive recrystallisations from an 8:2 mixture of ethyl acetate and acetone, and from butanol, melts at 135°–136°, are obtained.

Analysis:
| | | | | | |
|---|---|---|---|---|---|
| Calculated %: | C 58.12 | N 5.61 | N 6.78 | Cl 17.16 | F 4.60 |
| Found %: | 58.26 | 6.03 | 6.82 | 17.06 | 4.70 |
| | 58.27 | 5.94 | 6.81 | 17.18 | 4.75 |

The NMR spectrum confirmed the structure of the compound.

EXAMPLE 6:
N-[(1-m-fluorobenzyl-pyrrolidinyl-2)-methyl]-2-methoxy-5-sulphamoyl-benzamide

[(I)

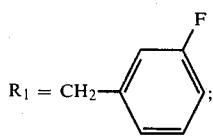

$R_2$=SO$_2$NH$_2$; code number: SL-D.193]

A mixture of 6.85 g (0.0219) mol of 2-methoxy-5-sulphamoyl-N-(pyrrolidinyl-2-methyl)-benzamide, 2.76 g (0.0200 mol) of potassium carbonate, 200 ml of acetone and a crystal of potassium iodide is heated to the reflux temperature. Thereafter a solution of 2.95 g (0.0204 mol) of m-fluorobenzyl chloride in 25 ml of acetone is introduced dropwise over the course of one hour. The solution is kept refluxing for a further 3 hours and is then filtered hot, the precipitate is rinsed twice with 100 ml of acetone at a time, and the filtrates are combined and concentrated to dryness. 4 g of crystals are obtained, and are triturated in ether, filtered off and dried in a desiccator under reduced pressure. The compound is purified by passing it over a silica column (eluant: acetone) and is finally recrystallised from ethanol in the presence of active charcoal.

2.0 g (yield=24%) of N-[(1-m-fluorobenzyl-pyrrolidinyl-2)-methyl]-2-methoxy-5-sulphamoyl-benzamide, melting at 166°, are thus obtained.

Analysis:
| | | | | |
|---|---|---|---|---|
| Calculated %: | C 56.99 | H 5.74 | N 9.97 | S 7.61 |
| Found %: | 56.71 | 5.89 | 9.82 | 7.62 |
| | 56.65 | 5.92 | 9.82 | 7.63 |

The NMR spectrum confirmed the structure of the compound.

EXAMPLE 7:
N-[1-(2-cyanoethyl)-pyrrolidinyl-2-methyl]-2-methoxy-5-sulphamoyl-benzamide

[(II); $R_1$=—CH$_2$—CH$_2$—CN: $R_2$=SO$_2$NH$_2$; code number: SL-C.262]

7.8 g (0.025 mol) of N-(pyrrolidinyl-2-methyl)-2-methoxy-5-sulphamoyl-benzamide are added to a stirred solution of 500 ml of acrylonitrile (sic), and the mixture is heated to the reflux temperature for 30 minutes. The solution is then evaporated to dryness under reduced pressure and the residue is crystallised by trituration with petroleum ether and is filtered off, dried in an oven and recrystallised successively from a mixture of acetone and other and from ethanol.

6.8 g (yield=74%) of N-[1-(2-cyanoethyl)-pyrrolidinyl-2-methyl]-2-methoxy-5-sulphamoyl-benzamide, melting at 142°, are thus obtained.

Analysis:
| | | | | |
|---|---|---|---|---|
| Calculated %: | C 52.44 | H 6.05 | N 15.29 | S 8.75 |
| Found %: | 52.55 | 6.09 | 15.09 | 8.89 |
| | 52.45 | 6.10 | 15.22 | 8.83 |

The NMR spectrum confirmed the structure of this compound.

EXAMPLE 8:
1(—)-N-[(1-α-methylbenzyl-pyrrolidinyl-2-)-methyl]-2-methoxy-5-sulphamoyl-benzamide and its hydrochloride

[(I);

$R_2$=SO$_2$NH$_2$; 1(—) compound; code number: SL-D.222]

(a) 25 g (0.206 mol) of d-(+)-α-methylbenzyl-amine, 16.87 g (0.196 mol) of 2-oxo-tetrahydrofurane and a few crystals of hydroquinone are introduced, under a nitrogen atmosphere, into a pressure-resistant 125 ml vessel. The mixture is heated to 250° for 12 hours and the solid residue is collected and distilled. 29.5 g (yield=79.8%) of d(+)-1-(α-methylbenzyl)-2-oxo-pyrrolidine are thus obtained. Boiling point=105°/0.05 mm Hg, [α]$_D$=+138.8° (dimethylformamide, C=5).

(b) 28.5 g (0.15 mol) of the preceding compound and 18.9 g (0.15 mol) of methyl sulphate are introduced into a 250 ml Erlenmeyer flask. The mixture is kept at 60° for 2 hours and then cooled in a bath of iced water, and a solution of sodium methylate (prepared from 3.45 g (0.15 mol) of sodium and 50 ml of methanol) is added gradually thereto. The mixture is stirred for 2 hours at ambient temperature and cooled in ice, and 13.7 g (0.227 mol) of nitromethane are then added dropwise. The reaction mixture is left to stand for 24 hours and is then poured into iced water, the whole is stirred vigorously and the crystals formed are filtered off, washed several times with water and then with ether, and dissolved in chloroform. The organic phase is dried over magnesium sulphate and evaporated, and the residue is recrystallised from isopropanol.

19.9 g (yield=57.2%) of d-(+)-1-(α-methylbenzyl)-2-nitromethylene-pyrrolidine melting at 123° are thus obtained.

$[\alpha]_D = +297.60°$ (dimethylformamide, c=5).

(c) A suspension of 18.8 g (0.0809 mol) of the preceding compound in 200 ml of methanol is hydrogenated under atmospheric pressure and at ambient temperature, in the presence of Raney nickel. After stirring for 3 hours, the catalyst is filtered off, the solvent is evaporated and the oily residue is distilled.

10.15 g (yield=62.3%) of 1-(−)-1-(α-methylbenzyl)-2-aminomethyl-pyrrolidine boiling at 98° under a pressure of 0.05 mm of mercury are thus obtained. $[\alpha]_D = -32.1°$ (dimethylformamide, c=5).

(d) 9.1 g (0.044 mol) of the preceding amine and 6.7 g of potassium carbonate suspended in 100 ml of anhydrous acetone are introduced into an Erlenmeyer flask. A solution of 11 g (0.044 mol) of 2-methoxy-5-sulphamido-benzoyl chloride in 100 ml of acetone is added dropwise with vigorous stirring at a temperature not exceeding +10°. The reaction mixture is stirred for 4 hours at ambient temperature and is then evaporated to dryness under reduced pressure at a temperature not exceeding 30°. The oily residue is washed with water and extracted with chloroform, the organic phase is treated with active charcoal and dried over magnesium sulphate, and the solvent is evaporated. The solid residue is triturated in benzene and is then recrystallized successively from benzene and from ethyl acetate.

6.9 g (yield=37.7%) of 1(−)-N-[(1-α-methylbenzyl-pyrrolidinyl-2)-methyl]-2-methoxy-5-sulphamido-benzamide melting at 129°–129.5° are thus obtained.

Analysis:

| | C 60.41 | H 6.52 | H 10.06 | S 7.68 |
|---|---|---|---|---|
| Calculated %: | | | | |
| Found %: | 60.62 | 6.84 | 10.08 | 7.48 |
| | 60.31 | 6.66 | 10.05 | 7.38 |

The NMR spectrum confirms the structure of the compound.

(e) The hydrochloride of the preceding base is prepared by adding 0.1 N hydrochloric acid to this base. $[\alpha]_D = 78.69°$ (dimethylformamide, c=0.6).

Table I which follows shows the compounds of Examples 1 to 8 as well as other compounds which were prepared by applying the processes used in the Examples.

Table I

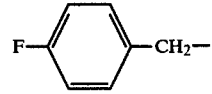

| Example | Code No. | n | $R_1$ | $R_2$ | $R_3$ | Characteristics M.p. in °C. b = base cl = hydrochloride |
|---|---|---|---|---|---|---|
| 1 | SL-C.205 | 1 | 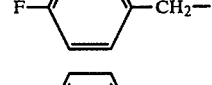 F—⌬—CH₂— | SO₂NH₂ | H | 202.5–203 |
| 1a | SL-C.205 dextrorotatary | 1 | F—⌬—CH₂— | SO₂NH₂ | H | 144–145 |
| 1b | SL-C.205 laeyorotatary | 1 | F—⌬—CH₂— | SO₂NH₂ | H | 143.5–144.5 |
| 2 | SL-C.161 | 1 | Cl—⌬—CH₂— | SO₂NH₂ | H | 211 |
| 3 | SL-C.189 | 2 | C₆H₅CH₂ | SO₂NH₂ | H | |
| 4 | SL-C.243 | 1 | C₆H₅CH₂ | SO₂NH₂ | CH₃ | |
| 5 | SL-D.165 | 1 | 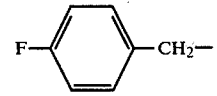 F—⌬—CH₂— | Cl | H | cl 135–136 |

Table I-continued $$\text{Structure: } R_2\text{-substituted phenyl with OCH}_3\text{, CO-NR}_3\text{-CH}_2\text{-CH(pyrrolidine-(CH}_2)_n\text{, N-R}_1)$$

Characteristics
M.p. in °C.
b = base
cl = hydrochloride

| Example | Code No. | n | R₁ | R₂ | R₃ | chloride |
|---|---|---|---|---|---|---|
| 6 | SL-D.193 | 1 | 3-F-C₆H₄-CH₂- | SO₂NH₂ | H | b 166 |
| 7 | SL-C.262 | 1 | CNCH₂CH₂- | SO₂NH₂ | H | b 142 |
| 8 | SL-D.222 l(−) | 1 | C₆H₅-CH(CH₃)- | SO₂NH₂ | H | b 129-129.5 |
| 9 | SL-C.017 | 1 | C₆H₅CH₂- | SO₂NH₂ | H | |
| 10 | SL-C.036 | 1 | cyclopropyl-CH₂- | SO₂NH₂ | H | b 157<br>cl 231-232 |
| 11 | SL-C.144 | 1 | C₆H₅CH₂- | SO₂N(CH₃)₂ | H | |
| 12 | SL-C.145 | 1 | C₆H₅CH₂- | Cl | H | |
| 13 | SL-C.152 | 1 | C₆H₅CH₂CH₂- | SO₂NH₂ | H | b 150<br>cl 233-234 |
| 14 | SL-C.155 | 1 | C₆H₅CH₂- | SO₂CH₃ | H | |
| 15 | SL-C.162 | 1 | 4-CH₃O-C₆H₄-CH₂- | SO₂NH₂ | H | b 172-173 |
| 16 | SL-C.188 | 1 | 3-OCH₃-C₆H₄-CH₂- | SO₂NH₂ | H | b 152-153 |
| 17 | SL-C.191 | 1 | 2-OCH₃-C₆H₄-CH₂- | SO₂NH₂ | H | b 166.5-167 |
| 18 | SL-C.193 | 1 | 3-Cl-C₆H₄-CH₂- | SO₂NH₂ | H | b 167-168 |
| 19 | SL-C.195 | 1 | 4-CH₃-C₆H₄-CH₂- | SO₂NH₂ | H | b 185-186 |
| 20 | SL-C.196 | 1 | 2-Cl-C₆H₄-CH₂- | SO₂NH₂ | H | b 209-210 |
| 21 | SL-C.204 | 1 | 4-Cl-C₆H₄-CH₂CH₂- | SO₂NH₂ | H | b 177 |

Table I-continued

General structure: benzamide with $R_2$ substituent, $OCH_3$ group, $CO-NR_3-CH_2-$ linker to pyrrolidine ring with $(CH_2)_n$ and $N-R_1$.

| Example | Code No. | n | $R_1$ | $R_2$ | $R_3$ | Characteristics M.p. in °C. b = base cl = hydrochloride |
|---|---|---|---|---|---|---|
| 22 | SL-C.213 | 1 | $CH_3$ (with benzyl $CH_2-$) | $SO_2NH_2$ | H | b 177.5 |
| 23 | SL-C.299 | 1 | $CH\equiv C-CH_2-$ | $SO_2NH_2$ | H | cl 214 |
| 24 | SL-D.090 | 1 | $(C_6H_5)_2CH-$ | $SO_2NH_2$ | H | cl >260 |
| 25 | SL-D.163 | 1 | 4-F-$C_6H_4$-$CH_2-$ | $SO_2CH_3$ | H | b 100–100.5 |
| 26 | SL-D.192 | 1 | 2-F-$C_6H_4$-$CH_2-$ | $SO_2NH_2$ | H | b 183 |
| 27 | SL-D.194 | 1 | 4-F-$C_6H_4$-$CH=CH-CH_2-$ | $SO_2NH_2$ | H | b 172 |
| 28 | SL-D.223 d(+) | 1 | $C_6H_5-CH(CH_3)-$ | $SO_2NH_2$ | H | b 127–128 cl 218–220 (decomposition) $[\alpha]_D = +78°$ (DMF c = 0.6) |
| 29 | SL-D.296 | 1 | 4-F-$C_6H_4$-$CH_2$ | $SO_2H(CH)_2$ | H | cl 209–210 |

The starting compounds (II) as well as the intermediate compounds used for their preparation are described in the tables which follow.

Table II

Structure (III): pyrrolidine ring with $(CH_2)_n$, $N-R_1$, and $-CH_2-NH-R_3$ substituent.

| $R_1$ | $R_3$ | n | Physical characteristics | C % Calc. | C % Found | H % Calc. | H % Found | N % Calc. | N % Found |
|---|---|---|---|---|---|---|---|---|---|
| $CH_2$-cyclopropyl | H | 1 | boiling point = 58–60°/0.25 mm | 70.08 | 70.21 | 11.76 | 12.06 | 18.16 | 18.15 |
| $CH_2-CH_2-C_6H_5$ | H | 1 | boiling point = 79–80°/0.01 mm | 76.42 | 76.21 76.20 | 9.87 | 9.93 9.84 | 13.71 | 13.85 13.70 |

Table II-continued $$\underset{R_1}{N}\underset{|}{\overset{(CH_2)_n}{\diagdown}}\underset{R_3}{CH_2-NH} \quad (III)$$

| R₁ | R₃ | n | Physical characteristics | C % Calc. | C % Found | H % Calc. | H % Found | N % Calc. | N % Found |
|---|---|---|---|---|---|---|---|---|---|
| CH₂—⟨C₆H₄⟩—CCH₃ (para) | H | 1 | boiling point = 110–114°/0.02 mm | 70.87 | 71.39 / 71.04 | 9.15 | 9.19 / 9.28 | 12.71 | 12.85 / 12.86 |
| CH₂—⟨C₆H₄⟩—CCH₃ (meta) | H | 1 | boiling point = 119–121°/0.05 mm | 70.87 | 70.75 | 9.15 | 9.20 | 12.71 | 12.95 |
| CH₂—⟨C₆H₄⟩—CCH₃ (ortho) | H | 1 | boiling point = 106–108°/0.01 mm | 70.87 | 70.79 | 9.15 | 9.20 | 12.71 | 12.81 |
| CH₂—⟨C₆H₄⟩—Cl (ortho) | H | 1 | boiling point = 110–111°/0.03 mm | | | | | | |
| CH₂—⟨C₆H₄⟩—Cl (meta) | H | 1 | boiling point = 95–96°/0.03 mm (impure product) | | | | | | |
| CH₂—CH₂—⟨C₆H₄⟩—Cl | H | 1 | boiling point = 133–134°/0.2 mm | 65.40 | 64.90 / 65.02 | 8.02 | 8.01 / 7.99 | 11.73 | 11.50 / 11.50 |
| CH₂—⟨C₆H₄⟩—CH₃ | H | 1 | boiling point = 106°/0.2 mm | 76.42 | 76.77 / 76.72 | 9.87 | 9.81 / 9.75 | 13.71 | 13.75 |
| CH₂—⟨C₆H₄⟩—CF₃ | H | 1 | boiling point = 99–100°/0.2 mm | 60.45 | 60.66 / 60.45 | 6.63 | 6.64 / 6.69 | 10.85 | 10.83 / 10.86 |

Table III $$\underset{R_1}{N}\underset{|}{\overset{(CH_2)_n}{\diagdown}}=CHNO_2$$

| R₁ | n | Physical characteristics | C % Calc. | C % Found | H % Calc. | H % Found | N % Calc. | N % Found |
|---|---|---|---|---|---|---|---|---|
| —CH₂—cyclopropyl | 1 | melting point = 84° | 59.32 | 59.26 / 59.13 | 7.74 | 7.86 / 7.77 | 15.37 | 15.23 / 15.24 |
| CH₂—CH₂—C₆H₅ | 1 | melting point = 114.5–115° | 67.22 | 67.25 / 67.46 | 6.94 | 7.12 / 7.06 | 12.06 | 11.94 / 12.00 |

Table III-continued $$\underset{R_1}{N}\overset{(CH_2)_n}{\diagdown}=CHNO_2$$

| R₁ | n | Physical characteristics | C % Calc. | C % Found | H % Calc. | H % Found | N % Calc. | N % Found |
|---|---|---|---|---|---|---|---|---|
| —CH₂—C₆H₄—OCH₃ (para) | 1 | melting point = 136° | 62.89 | 62.73 / 62.77 | 6.50 | 6.66 / 6.61 | 11.28 | 11.20 / 11.21 |
| —CH₂—C₆H₄—OCH₃ (meta) | 1 | melting point = 90–91° | 62.89 | 62.88 / 62.86 | 6.50 | 6.59 / 6.41 | 11.28 | 11.39 |
| —CH₂—C₆H₄—OCH₃ (ortho) | 1 | melting point = 166–167° | 62.89 | 62.97 | 6.50 | 6.52 | 11.28 | 11.26 |
| —CH₂—C₆H₄—Cl (ortho) | 1 | melting point = 166° | 57.04 | 57.28 | 5.19 | 5.36 | 11.09 | 11.35 |
| —CH₂—C₆H₄—Cl (meta) | 1 | melting point = 133° | 57.04 | 57.12 / 57.28 | 5.19 | 5.07 / 5.17 | 11.09 | 11.22 |
| —CH₂—CH₂—C₆H₄—Cl (para) | 1 | melting point = 112° | | | | | | |
| —CH₂—C₆H₄—CH₃ (para) | 1 | melting point = 102° | | | | | | |
| —CH₂—C₆H₄—CF₃ (para) | 1 | melting point = 133.5 | 54.55 | 54.57 / 54.34 | 4.58 | 4.61 / 4.62 | 9.79 | 9.74 |

Table IV $$\underset{R_1}{N}\overset{(CH_2)_n}{\diagdown}=O$$

| R₁ | n | Physical characteristics | C% Calc. | C% Found | H% Calc. | H% Found | N% Calc. | N% Found |
|---|---|---|---|---|---|---|---|---|
| —CH₂—cyclopropyl | 1 | boiling point = 90–91°/0.15 mm | 69.02 | 68.78 / 68.90 | 9.41 | 9.58 / 9.64 | 10.06 | 9.98 / 10.10 |
| —CH₂—C₆H₄—OCH₃ (para) | 1 | boiling point = 148–152°/0.02 mm | 70.22 | 70.45 / 70.23 | 7.37 | 7.36 / 7.17 | 6.82 | 6.81 / 6.78 |

Table IV-continued

| R₁ | n | Physical characteristics | C% Calc. | C% Found | H% Calc. | H% Found | N% Calc. | N% Found |
|---|---|---|---|---|---|---|---|---|
| —CH₂—C₆H₄—OCH₃ (para) | 1 | boiling point = 164–166°/0.1 mm | 70.22 | 70.35 | 7.37 | 7.35 | 6.82 | 6.80 |
| —CH₂—C₆H₄—OCH₃ (ortho) | 1 | boiling point = 135–138°/0.01 mm | 70.22 | 70.41 | 7.37 | 7.29 | 6.82 | 6.79 |
| —CH₂—C₆H₄—Cl (ortho) | 1 | boiling point = 121–123°/0.03 mm | | | | | | |
| —CH₂—C₆H₄—Cl (para) | 1 | boiling point = 140–141°/0.03 mm | | | | | | |
| —CH₂—CH₂—C₆H₄—Cl | 1 | melting point = 74.5° | | | | | | |
| —CH₂—C₆H₄—CH₃ | 1 | boiling point = 135–136°/0.15 mm | 76.16 | 76.16 | 7.99 | 7.96 | 7.40 | 7.28 |
| —CH₂—C₆H₄—CF₃ | 1 | boiling point = 122–124°/0.2 mm | 59.22 | 59.35 / 59.35 | 4.97 | 4.93 / 5.06 | 5.76 | 5.85 / 5.88 |

After determination of their acute toxicity, the compounds of the invention were subjected to a series of neuro-pharmacological tests which revealed their valuable psychotropic properties.

The compounds were administered in the form of their hydrochlorides or of their methanesulphonates.

The reference substance chosen was N-[(1-ethylpyrrolidinyl-2)-methyl]-2-methoxy-5-sulphamoyl-benzamide hydrochloride or Sulpiride HCl.

The acute toxicity was evaluated in Swiss CD1 mice of both sexes, of average weight 20 g. The 50% lethal dose (LD 50) of each product was determined by a graphical method.

Table V

| Compounds (cl = hydrochloride ms = methanesulphenate) | Acute toxicity in mice method of administration | LD 50 (mg/kg) over 48 hours |
|---|---|---|
| Sl-C.262 (cl) | intraperitoneal | >2,000 |
| SL-C.299 (cl) | intraperitoneal | 170 |
| Sl-D.090 (cl) | intraperitoneal | >1,500 |
| SL-D.163 (cl) | intraperitoneal | 400 |
| SL-D.165 (cl) | intraperitoneal | 275 |

Table V-continued

| Compounds (cl = hydrochloride ms = methanesulphenate) | Acute toxicity in mice method of administration | LD 50 (mg/kg) over 48 hours |
|---|---|---|
| SL-D.192 (cl) | intraperitoneal | >2,000 |
| SL-D.193 (cl) | intraperitoneal | >2,000 |
| SL-D.194 (cl) | intraperitoneal | >2,000 |
| SL-D.222 (cl) | intrapertoneal | 625 |
| SL-D.223 (cl) | intraperitoneal | 650 |
| SL-C.205 (racemic)(cl) | intraperitoneal | 750 |
| SL-C.205 (racemic)(cl) | oral | >3,000 (7 days) |
| SL-C.205 (racemic)(ms) | intravenous | 190 |
| SL-C.205 l (ms) | intravenous | 160 |
| SL-C.205 d (ms) | intravenous | 160 |
| Sulpiride (cl) | intraperitoneal | 170 |
| Sulpiride (cl) | oral | 2,250 (7 days) |

The neuro-pharmacological activity was studied with the aid of the following three tests:

(1) Antagonism towards stereotypies induced by apomorphine in male Sprague-Dawley (Charles River) rats of average weight 130 g, in accordance with the method of Janssen and colleagues (Arzneim. Forsch. 1960, 10, 1003).

(2) Catalepsy-inducing effect in rats of the same species and of the same weight, in accordance with the method of Tedeschi and colleagues (Arch. Intern. Pharmacodyn. 1959, 122, 129).

In these two tests, the results are expressed by the 50% active doses (AD 50).

(3) Protection against a stress due to an environment and due to new feedstuffs, in male rats (CDI strain, weight about 20 g) in accordance with the method of Stephens (Brit. J. Pharmacol. 1973, 49, 146 P.). The doses (AD 40) which produce a 40% increase in the feedstuff taken were determined. The results are summarised in Table VI.

Table VI

| Compounds (cl) = hydrochloride (ms) = methanesulphonate | Antagonism to stereotypies induced by apomorphine in rats | |
|---|---|---|
| | AD 50, kg/kg | method of administration |
| SL-C.299 (cl) | 80 | intraperitoneal |
| SL-D.163 (cl) | 3 | intraperitoneal |
| SL-D.165 (cl) | 1.5 | intraperitoneal |
| SL-D.193 (cl) | 150 | intraperitoneal |
| SL-C,205, racemic (cl) | 30 | intraperitoneal |
| SL-C.205, racemic (cl) | 85 | oral |
| SL-C.205, racemic (ms) | 75 | oral |
| SL-C.205 l (ms) | >150* | oral |
| SL-C.205 d (ms) | 50 | oral |
| Sulpiride (cl) | 60 | intraperitoneal |
| Sulpiride (cl) | >600 | oral |

The results obtained for the Kydel chlorides are given in weight of base
*=no activity was observed up to this dose Table VII

| Compounds (cl) = hydrochloride | Catalepsy-inducing effect in rats AD 50, kg/kg administered intraperitoneally |
|---|---|
| SL-C.299 (cl) | >150 |
| Sl-C.193 (cl) | >300 |
| SL-C.205 (cl) | >480 |
| Sulpiride (cl) | >100* |

*Sulpiride could not be administered at a higher dose, in view of its toxicity.

Table VIII

| Compounds (cl) = hydrochloride (ms) = methanesulphonate | Protection against stress in mice - AD 40 for oral administration (mg/kg) |
|---|---|
| SL-D.165 (cl) | 30 |
| SL-D.192 (cl) | 30 |
| SL-D.193 (cl) | 30 |
| SL-C.205, racemic (ms) | 60 |
| SL-C.205 l (ms) | >30* |
| SL-C.205 d (ms) | 30 |

*no activity was observed up to this dose.

Examination of the results shows that the compounds of the invention are psychotropic agents.

Compound SL-C.205, in particular, is much less toxic but markedly more active, than Sulpiride. In particular, whilst it does not induce catalepsy up to high doses, it is a powerful antagonistic agent, even when administered orally, to stereotypies induced in rats by apomorphine, whilst Sulpiride is inactive when administered by this route. The therapeutic margin of SL-C.205 is considerable.

Furthermore, it may be noted that the leavo-rotatary and dextre-rotatary isomers differ in respect of their activity; in fact, the leavo-rotatary isomer proves practically inactive in neuro-pharmacological tests, whilst the dextro-rotatary isomer has an activity 1.5 times or twice (depending on the chosen method of evaluation) as strong as that of the racemic compound.

Accordingly, this isomer can be used:

(a) at low or medium doses, advantageously because of its improved therapeutic index relative to that of the racemate, as a psychotropic medicament in the treatment of (1) anxiety conditions of various psychosomatic disturbances, such as gastro-duodenal ulcers, migraine and vertigos, and (2) depressive and psychopathological disturbances, especially during senescence, and (b) at higher doses, in psychotic disturbances such as serious behavioural disturbances, deliria and obsessional neuroses.

The compounds of the general formula (I) can be used as psychotropic medicaments in the treatment of various psychosomatic disturbances, such as gastro-duodenal ulcers, migraine and vertiges, in depressive and psychopathological disturbances, especially of senescence, and, at higher doses, is psychotic disturbances such as serious behavioural disturbances, deliria and obsessional neuroses.

Consequently, the invention comprises all pharmaceutical compositions which contain the compounds (I) and their salts as active principles, in combination with any excipients suitable for their oral, endo-rectal or parenteral administration. These pharmaceutical compositions can also contain other medicamentous substances with which the compounds (I) are pharmaceutically and therapeutically compatible.

For oral administration, all pharmaceutical forms suitable for this method of administration are used, that is to say tablets, dragées, gelatine-coated pills, capsules, cachets and potable solutions and suspensions; the unit dose of compound (I) can vary between 5 mg and 200 mg and the daily dose is between 10 mg and 400 mg.

For endo-rectal administration, suppositories containing 10 to 200 mg of compound (I) and administered to the patient at the rate of 1 to 3 per 24 hours are used.

For parenteral administration, injectable and buffered solutions, prepared beforehand or at the time of use, are employed. The dose per unit administration can vary between 5 and 100 mg and the daily dose is between 5 and 300 mg.

We claim:

1. A compound of the formula:

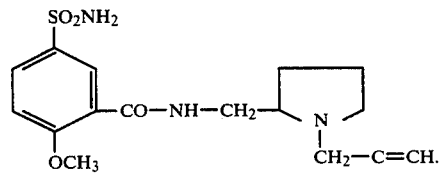

2. A pharmaceutical agent capable of treating nervous and psychosomatic disorders which comprises an effective amount of the compound of claim 1 for treating said nervous and psychosomatic disorders and a compatible pharmaceutically acceptable carrier.

3. A method of combatting nervous and psychosomatic disorders in a patient which comprises administering to said patient said pharmaceutical agent of claim 2.

* * * * *

UNITED STATES PATENT AND TRADEMARK OFFICE
CERTIFICATE OF CORRECTION

PATENT NO. : 4,189,495
DATED : February 19, 1980
INVENTOR(S) : KAPLAN et al

It is certified that error appears in the above-identified patent and that said Letters Patent are hereby corrected as shown below:

In claim 1, in the formula, change "$CH_2-C=CH$"

to $--CH_2-C\equiv CH--$

Signed and Sealed this

Twentieth Day of May 1980

[SEAL]

Attest:

SIDNEY A. DIAMOND

*Attesting Officer*     *Commissioner of Patents and Trademarks*